United States Patent [19]
Lapinet et al.

[11] 3,978,213
[45] Aug. 31, 1976

[54] COSMETIC USE OF CYCLIC AMP AND PHOSPHODIESTERASE INHIBITORS

[75] Inventors: Eugene Lapinet, Paris, France; Georges D. Cehovic, Santa Ana, Calif.; Theodore Z. Posternak, Geneva, Switzerland

[73] Assignee: Nelson Research & Development Company, Irvine, Calif.

[22] Filed: Jan. 3, 1975

[21] Appl. No.: 538,395

Related U.S. Application Data

[63] Continuation-in-part of Ser. No. 270,070, July 10, 1972, abandoned, which is a continuation-in-part of Ser. No. 111,623, Feb. 1, 1971, abandoned.

[52] U.S. Cl............................ 424/180; 424/253; 424/358
[51] Int. Cl.$^2$............. A61K 7/00; A61K 31/52; A61K 31/705
[58] Field of Search ........... 424/62, 180, 253, 358; 260/112 R, 211.5 R

[56] References Cited
UNITED STATES PATENTS

| | | | |
|---|---|---|---|
| 3,558,595 | 1/1971 | Jones | 260/211.5 R |
| 3,712,885 | 1/1973 | Weiman | 260/211.5 R |

FOREIGN PATENTS OR APPLICATIONS

| | | | |
|---|---|---|---|
| 2,883M | 11/1964 | France | 424/180 |
| 1,440,795 | 4/1966 | France | 424/180 |

OTHER PUBLICATIONS

Butcher, The J. of Biol. Chem., vol. 237, Apr., 1962, pp. 1244–1250.

*Primary Examiner*—James O. Thomas, Jr.
*Assistant Examiner*—A. P. Fagelson
*Attorney, Agent, or Firm*—Martin A. Voet

[57] ABSTRACT

Methods and compositions designed for dermatological and cosmetic use containing as an active ingredient, cyclic 3',5'-adenosine monophosphate and salts thereof and optionally, a phosphodiesterase inhibitor such as theophylline.

2 Claims, No Drawings

COSMETIC USE OF CYCLIC AMP AND PHOSPHODIESTERASE INHIBITORS

RELATION TO EARLIER APPLICATIONS

This application is a continuation-in-part of U.S. application Ser. No. 270,070 filed July 10, 1972, now abandoned, which in turn was a continuation-in-part of U.S. application Ser. No. 111,623 filed Feb. 1, 1971, now abandoned.

BACKGROUND OF THE INVENTION

1. Field of the Invention

The present invention generally relates to compositions and methods for dermatological use. More particularly, the present invention relates to compositions and methods for human cosmetic use.

2. Background of the Invention

During the last few years, the biological role of cyclic 3',5'-adenosine monophosphate (cyclic AMP) has been the subject of a great number of studies. Cyclic AMP appears to be involved in the regulation of function and metabolism of a large variety of tissues and has been identified as a "second messenger" in the concept of hormone action by Sutherland (*Harvey Lectures*, 57, 17 (1962); *Circulation*, 37, 279 (1968)).

It is also known that body enzymes known as phosphodiesterases inactivate cyclic AMP by converting it to 5'-adenosine monophosphate.

Cyclic AMP has the following chemical structure:

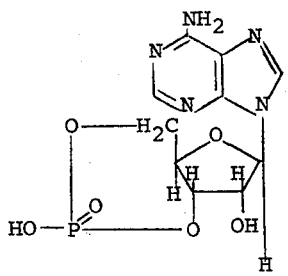

SUMMARY OF THE INVENTION

It has now been discovered that topical compositions containing an active ingredient cyclic AMP or salts thereof may be advantageously applied to human skin to temporarily soothe and soften skin which has become dry and/or wrinkled e.g. caused by age or weather. The composition of the present invention also has a soothing, emollient effect and may have a minor anti-inflammatory effect on skin which has become chapped or reddened by minor irritations caused by excessive exposure to sun or wind. Generally, the topical compositions are applied in conventional amounts about one to about three times daily.

It also has been discovered that enhanced results may be obtained by periodic interruption of treatment, e.g. daily application for about a week followed by a week of no treatment, followed by a week of daily application, etc.

The active ingredient which may be used in the present invention is cyclic 3',5'-adenosine monophosphate (cyclic AMP) or salts thereof e.g. the sodium salt in amounts ranging from about 0.01 to about 2% by weight of the composition.

In addition to the active ingredients discussed above, it has been found that about 0.1% to about 2% by weight of a compound which inhibits the enzymatic degradation of cAMP acts to prolong the effectiveness of the treatment described herein and acts to reduce the concentration of active ingredient otherwise needed. Compounds which block the enzymatic degradation of cAMP are known as phosphodiesterase inhibitors. Examples of non-toxic phosphodiesterase inhibitors which may be used in the invention include those cAMP derivatives known in the art as phosphodiesterase inhibitors, papaverine, and xanthines such as, for example, theophylline and caffein.

An effective amount of the active ingredient, together with phosphodiesterase inhibitor as desired, is admixed with a conventional non-toxic cosmetic carrier suitable for human dermatological use. For example, suitable conventional cosmetic carriers include combinations of petroleum waxes, stearin, glycerol, lanolin, sesame oil, lanette wax, propylene glycol, etc.

The preferred method of application is once, twice or three times daily of enough of the formulation to lightly cover the area to be treated. It has been found that improved results are obtained if, after a period of time, e.g., about 7–14 days, treatment is discontinued for about a week, and then the treatment cycle is repeated. It is not known why this method of application leads to improved results, but it is theorized that the skin cells may require periods of rest between periods of stimulation for the normal regenerative process of the body to act.

As indicated above, we have discovered that the compositions disclosed herein possess cosmetic properties which make them useful as dermatological compositions, such as ointments, creams, gels, lotions etc. intended for cosmetic care of the human skin. More particularly, the composition disclosed herein exhibit anti-phlogistic, skin softening and skin elasticity and moisture-increasing activities.

The following examples are given to illustrate the invention, but is should be understood that the examples are for the purpose of illustration and the invention is not to be regarded as limited to any of the specific materials therein. Unless otherwise indicated, "parts" and "%" are by weight.

EXAMPLE I

The following are examples of various cosmetic formulations for dermatological use:

| Formulation | | |
|---|---|---|
| A. | | |
| | Glycerol stearate | 13 |
| | Polyoxyethylene cetylic alcohol | 5 |
| | Glycerol | 7 |
| | Lanolin | 2 |
| | Cyclic 3',5'-adenosine monophosphate acid | 0.1 |
| | Water | 72.9 |
| B. | | |
| | Stearin | 10 |
| | Polyoxyethyleneglycol stearate | 5 |
| | Glycerol | 5 |
| | Perhydrosqualene | 5 |
| | Cyclic sodium 3',5'-adenosine monophosphate | 0.5 |
| | Water | 74.5 |

EXAMPLE II

The following cream formulation C was made and tested on humans.

| Formulation | |
|---|---|
| C. | |
| Lanol | 3.60 |
| Cetylic alcohol | 1.80 |
| Stearic acid | 10.20 |
| Stearic glycerol | 3.60 |
| Glycerin | 12.00 |
| Sodium benzoate | 1.20 |
| Sodium borate | 0.12 |
| Perhydrosqualene | 6.00 |
| Water | 59.42 |
| Preservatives | 0.36 |
| Lipoproteol | 1.20 |
| Theophylline | 0.4 |
| Cyclic sodium 3',5'-adenosine monophosphate | 0.1 |

Formulation C was applied to the faces and necks of 30 women ranging in age from 35 to 64. After 2–4 weeks of treatment, the women were each evaluated by skilled cosmeticians. It was concluded from the tests that the results obtained using the cream formulation were clearly superior to the results obtained with conventional formulations. That is, the skin of the women using the cream formulation was generally more elastic, softer and had a more youthful appearance. Small wrinkles around the neck were decreased in size or eliminated. In addition, the women reported that their skin felt softer and smoother and had an enhanced skin tone.

We claim:

1. A method of temporarily softening and enhancing the natural elasticity of the skin comprising applying topically to human skin a composition comprising from about 0.01 to about 2% by weight of a member selected from the group consisting of cyclic 3',5'-adenosine monophosphate and a cosmetically acceptable salt thereof, about 0.1 to about 2% by weight of a non-toxic inhibitor of phosphodiesterase and a suitable dermatological carrier.

2. A method of temporarily softening and enhancing the natural elasticity of the skin comprising applying topically to human skin a composition comprising about 0.01 to about 2% of the sodium salt of cyclic 3',5'-adenosine monophosphate, about 0.1 to about 2% theophylline together with a suitable dermatological carrier.

* * * * *